US00PP24384P3

(12) United States Plant Patent
Harris

(10) Patent No.: US PP24,384 P3
(45) Date of Patent: Apr. 15, 2014

(54) AZALEA PLANT NAMED 'MNIHAR026'

(50) Latin Name: ***Rhododendron* sp.**
Varietal Denomination: MNIHAR026

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 49 days.

(21) Appl. No.: 13/573,113

(22) Filed: Aug. 22, 2012

(65) Prior Publication Data

US 2014/0059725 P1 Feb. 27, 2014

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of azalea plant with spring and fall blooming, attractive, showy, hose-in-hose red-purple flowers, easily propagated by semi-hardwood cuttings in late spring through summer, moderate growth rate under normal fertilization and moisture conditions; compact, globose and freely-branching growth habit, grows well in containers, thrives in shade or sun and is hardy to Zone 6, is disclosed.

2 Drawing Sheets

Genus and species: *Rhododendron* sp.
Variety denomination: 'MNIHAR026'.

BACKGROUND OF THE NEW PLANT

The present invention is a new and distinct variety of evergreen azalea in the genus *Rhododendron*. This new azalea, hereinafter referred to as 'MNIHAR026', originated from a planned cross hybridization in 2001 between the female azalea plant 'Conlec' (U.S. Plant Pat. No. 10,580) and the male azalea plant 'September Morn' (unpatented) in a controlled environment in Lawrenceville, Ga. The present invention has a blooming period of April and late August until frost. 'MNIHAR026' has a compact, globose freely branching growth habit, and cold hardiness.

The new plant was first propagated via semi-hardwood cuttings in 2005 in Dearing, Ga. and has been asexually reproduced repeatedly by semi-hardwood cuttings in Dearing, Ga. for over 5 years, four generations. 'MNIHAR026' has been found to retain its distinctive characteristics through successive asexual propagations via semi-hardwood cuttings.

Plant Breeder's Rights for this variety have not been applied for. 'MNIHAR026' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, red-purple colored flowers;
3. Numerous hose-in-hose flowers;
4. Easily propagated by semi-hardwood cuttings in late spring through summer;
5. Moderate growth rate under normal fertilization and moisture conditions;

6. Compact, globose freely branching growth habit;
7. Grows well in containers;
8. Thrives in shade or sun; and
9. Hardy to Zone 6.

DESCRIPTION OF THE PHOTOGRAPHS

This new azalea hybrid is illustrated by the accompanying photographs. The colors shown are as true as can be reasonably obtained by conventional photographic means. The photographs are of four-year-old plants grown in filtered shade and full sun in 2010 and 2011 in Dearing, Ga.

DETAILED BOTANICAL DESCRIPTION OF THE NEW PLANT

Figure 1:
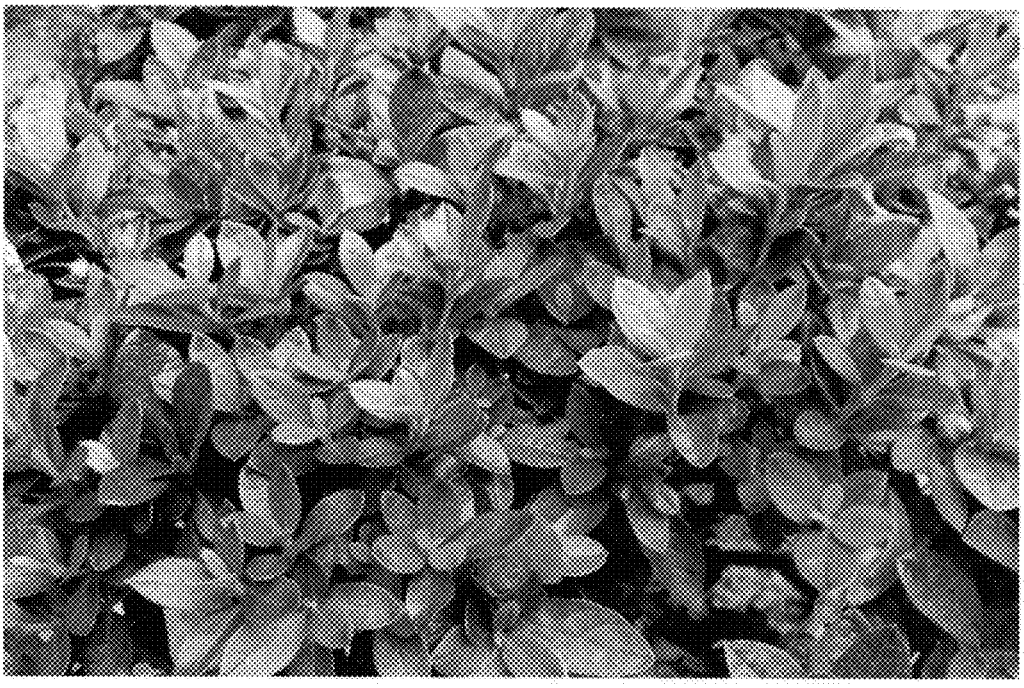
FIG. 1 shows a close-up of the flower buds and immature foliage.
Figure 2:
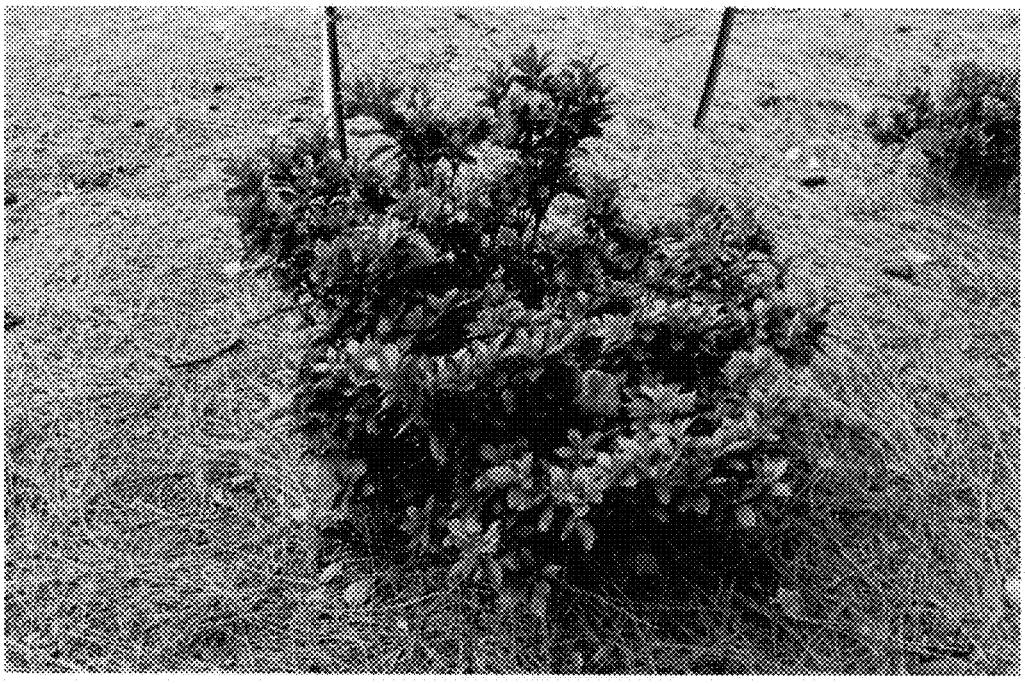
FIG. 2 shows mature foliage and growth habit and fall flowering.
Figure 3:
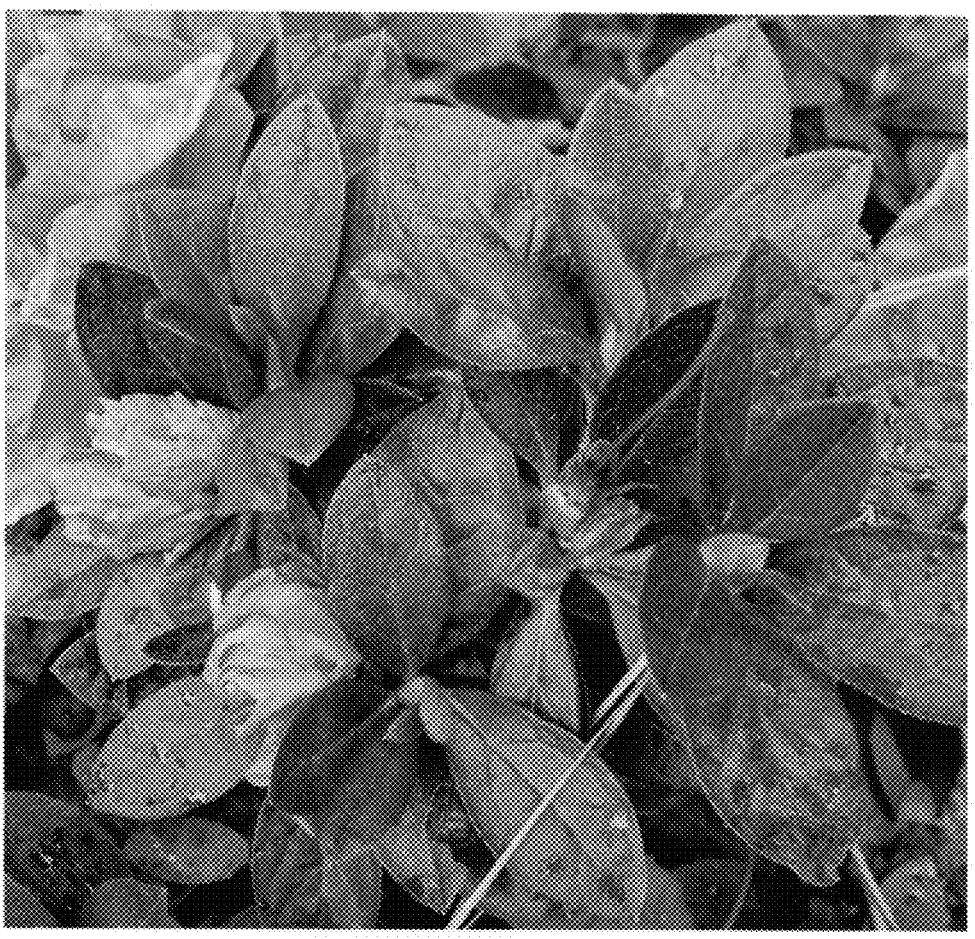
FIG. 3 shows a close-up of the flower buds and mature foliage.
Figure 4:
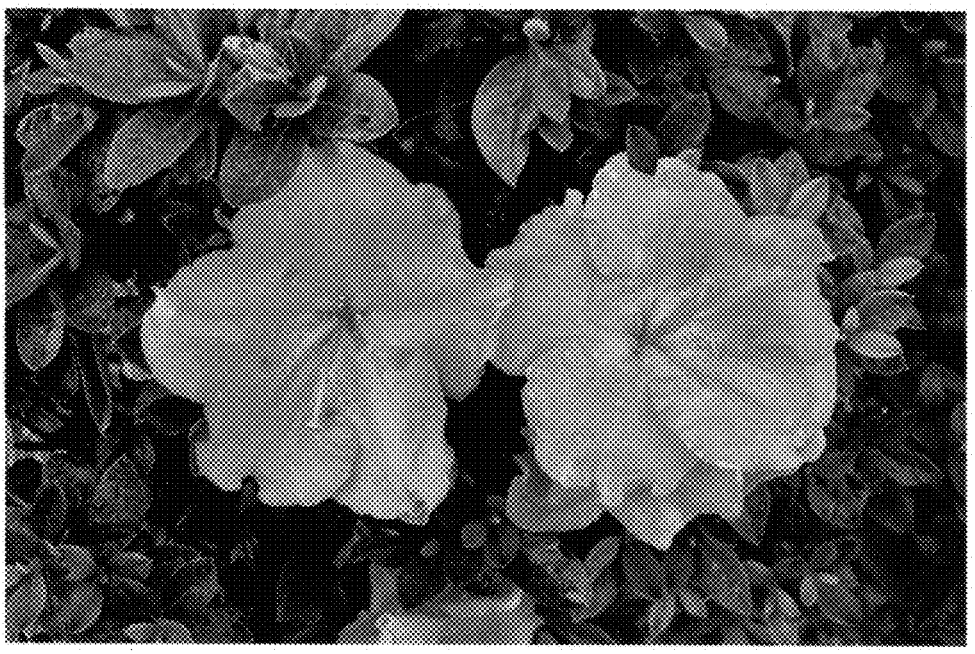
FIG. 4 shows a close-up of the flower size, form, and color.

The following is a detailed description of the new variety of azalea based on observations made of two and three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, 2010, 2011, and 2012. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Denomination*.—'MNIHAR026'.

Parentage:

*Female parent*.—The azalea plant 'Conlec' (U.S. Plant Pat. No. 10,580).

*Male parent*.—The azalea plant 'September Morn' (unpatented).

Plant:

*Form*.—Compact, globose.

*Texture*.—Medium.

*Height* (*mature plant*).—152.4 cm to 182.88 cm.

*Width* (*mature plant*).—167.64 cm to 213.36 cm.

*Growth habit*.—Freely branching; compact globose.

*Growth rate*.—Moderate growth rate under normal fertilization and moisture conditions. In a period of 5 years from a rooted cutting the plant reaches a height of 71.0 cm and a spread of 89.0 cm. The growth rate is normally averages about 13.0 cm per year; the plant reaches a height of 152.4 cm to 182.88 cm at maturity while maintaining a compact globose habit due to the abundant deliquescent branch development.

*Spring growth*.—The date of initial spring growth is March 26, followed by continuous growth through fall.

*Life cycle*.—Perennial evergreen.

Leaves:

*Arrangement*.—Alternate, simple.

*Shape*.—Elliptic.

*Apex*.—Acute.

*Base*.—Acute.

*Margin*.—Entire.

*Length*.—5.0 cm.

*Width*.—2.2 cm.

*Venation pattern*.—Pinnate; the mid-veins and laterals are impressed on the upper surface and are prominent on the lower surface. Mid-vein Color: Lower surface: RHS 146C (yellow-green). Upper surface: RHS 146C (yellow-green).

*Immature leaf*.—Upper surface: Color: Matte, RHS 144A (yellow-green). Pubescence: Strigose and scabrous. Color: RHS 164D (greyed-orange). Lower surface: Color: Matte, RHS 146C (yellow-green). Pubescence: Strigose. Color: RHS 155C (white).

*Mature leaf*.—Upper surface: Color: Semi-glossy to matte; RHS 147A (yellow-green). Pubescence: Strigose and scabrous. Color: RHS 165A (greyed-orange). Lower surface: Color: Matte, RHS 146B (yellow-green). Pubescence: Strigose. Color: RHS 164C (greyed-orange).

*Petiole*.—Length: 0.6 cm. Diameter: 0.125 cm by 0.15 cm. Pubescence: Strigose. Length: 0.1 cm. Color: Immature: RHS N155A (white). Mature: RHS 164D (greyed-orange). Color: Immature: RHS 146C (yellow-green). Mature: RHS 144A (yellow-green).

Stems:

*Form*.—Branched at terminal buds with some from auxiliary buds at leaf nodes.

*Young stems* (*actively growing, less than one year old*).—Color: RHS 144A (yellow-green). Pubescence: Strigose. Color: RHS N155A (white) maturing to RHS 165A (greyed-orange). Length of fully elongated flush: 3.7 cm on average. Diameter: 0.2 cm.

*Mature stems* (*one year old and older*).—Color: RHS N199C (grey-brown), RHS N199B (grey-brown) and RHSN200B (brown). Pubescence: Strigose, the quantity decreases with age of the stem. Color: RHS 165A (greyed-orange). Length: 14.0 cm on average for full year's growth. Diameter: 0.3 cm in second year. Pith: Solid and uniform. Internode length: Average 1.0 cm on actively growing vegetative stems.

Flower buds:

*Arrangement and form* (*at terminal end*).—Borne in groups of one to four, sheathed by zero or one modified leaf bracts.

*Bracts*.—Length: Average 2.3 cm. Width: 0.5 cm. Color: RHS 147A (yellow-green).

*Shape*.—Ovate.

*Apex*.—Acute.

*Base*.—Rounded.

*Length* (*at tight bud*).—1.6 cm.

*Diameter* (*at tight bud*).—0.9 cm.

*Scales*.—Color: Immature: RHS 144D (yellow-green). Mature: RHS 145A (yellow-green). Length: 1.3 cm. Diameter: 0.8 cm. Texture: Matte; strigose pubescence. Pubescence color: RHS 164A (greyed-orange).

*Pedicel*.—Length: 0.8 cm at point bud begins to open. Diameter: 0.175 cm. Texture: Pubescent, strigose. Pubescence color: RHS N155D (white) and RHS 164B (greyed-orange). Color: RHS 145A (yellow-green).

*Calyx*.—Modified to form lower perianth.

*Texture*.—Glabrous.

*Color*.—RHS 64B (red-purple) and RHS 65C (red-purple) along mid-rib.

*Sepals*.—Length: 4.5 cm. Diameter: 3.4 cm. Shape: undulate, slightly loabed.

Flowers:

*Type*.—Perfect, hose-in-hose flowers.

*Shape*.—Open funnel-shaped.

*Flowering habit and period*.—Borne on the current season's growth; three weeks beginning in April in Dearing, Ga.; flowering resumes late August and continues until frost which can be as late as November or December.

*Lastingness of flowers on the plant*.—3 to 5 days in the sun; 3 to 6 days in the shade.

*Fragrance*.—Absent.

*Persistance*.—Self cleaning.

*Diameter*.—8.0 cm.

*Depth*.—3.8 cm.

*Petals*.—Quantity per flower and arrangement: Five imbricate petals that are fused at the base and remain fused up to 2.5 cm from the base. Shape: Obovate. Apex: Rounded. Base: Fused. Margin: Entire, slightly undulate. Texture (both upper and lower surfaces): Glabrous. Length (petals without spots): 4.6 cm. Length (petals with spots): 4.4 cm. Width (petals without spots): 3.4 cm. Width (petals with spots): 3.4 cm. Color: Upper surface: RHS 64B (red-purple), spots on the upper surface of the petal are RHS 71A (red-purple). Lower surface: RHS 64B (red-purple), spots on the lower surface of the petal are not visible.

Reproductive parts:

*Pistil*.—Quantity and form: Single, non-petaloid. Length: 2.5 cm. Diameter: 0.08 cm.

*Stigma*.—Color: RHS 59A (red-purple). Diameter: 0.2 cm.

*Style color*.—RHS 63C (red-purple).

*Ovary*.—Tomentose pubescence RHS N155A (white) with 6 locules.

*Ovary color*.—RHS 141A (green).

*Stamens*.—Quantity: 6 or 7 per flower; non-petaloid. Length: Average 1.3 cm. Width: Average 0.5 cm. Color: RHS 63C (red-purple).

*Anther*.—Length: 0.3 cm. Width: 0.125 cm. Color: RHS 164C (greyed-orange). Pollen: Low amount. Color: RHS 155D (white).

Fruit and seed: Observed.

*Maturity*.—The capsule matures in about 6 months in Dearing, Ga. and the fruit set is moderate and contains approximately 100 to 200 non-winged seeds.

*Capsule*.—Length: 0.45 cm. Width: 0.3 cm. Color: RHS 146B (yellow-green).

CULTURE

'MNIHAR026' grows well in a wide range of conditions and tolerates sun to shade. 'MNIHAR026' prefers moist, well-drained soil that is rich in organic matter and responds well to mulching and medium applications of fertilizer. 'MNIHAR026' does best in soil with a pH of 5.0 to 5.5 and is propagated with semi-hardwood cuttings in late spring through the summer. 'MNIHAR026' root in five to six weeks with a high percentage of rooting (80% plus). Tissue culture is also an effective means of propagation of 'MNIHAR026'.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR026' is compared to parental varieties 'Conlec' (U.S. Plant Pat. No. 10,580) and 'September Morn' (unpatented).

TABLE 1

| Characteristic | 'MNIHAR026' | 'Conlec' | 'September Morn' |
|---|---|---|---|
| Plant Height (Mature) | 152.4 cm to 182.88 cm | 182.88 cm to 243.84 cm | 76.2 cm |
| Flower Diameter | 8.0 cm | 8.89 cm to 10.16 cm | 5.08 cm to 6.35 cm |
| Flower Form | hose-in-hose | Single | Single |
| Flower Color | Red-purple | Purple | Red |
| Bloom Period | April and late August until frost | April and late July until frost | Early April |
| Hardy Zone | 6 | 7 | 5 |
| Stamen Number | 6 to 7 | 8 to 10 | 5 |
| Stamen Type | Non-petaloid | Non-petaloid | Non-petaloid |

When 'MNIHAR026' is compared to the commercial variety 'Roblen' (U.S. Plant Pat. No. 16,248), 'MNIHAR026' has a compact globose growth habit with a height of 71.0 cm and a spread of 89.0 cm in 5 years, while 'Roblen' has a height of 91.44 cm and a spread of 60.96 cm in six years. Additionally, 'MNIHAR026' has hose-in-hose flowers, while 'Roblen' has single to semi-double flowers.

I claim:

1. A new variety of azalea plant named 'MNIHAR026' as herein shown and Described.

* * * * *